(12) United States Patent
Afonina et al.

(10) Patent No.: US 11,059,860 B2
(45) Date of Patent: Jul. 13, 2021

(54) BIOCIDAL PEPTIDE AND PREPARATION BASED THEREON

(71) Applicant: "VERTA RESEARCH-PRODUCTION COMPANY" LTD, St. Petersburg (RU)

(72) Inventors: Irina Vasil'evna Afonina, Sankt-Peterburg (RU); Alexandr Alexandrovich Kolobov, Sankt-Peterburg (RU); Nikolay Ivanovich Kolodkin, Sankt-Peterburg (RU); Mariya Pavlovna Smirnova, Sankt-Peterburg (RU); Ludmila Ivanovna Stefanenko, Pargolovo (RU)

(73) Assignee: VERTA RESEARCH-PRODUCTION COMPANY LTD, St. Petersburg (RU)

( * ) Notice: Subject to any disclaimer, the term of this patent is extended or adjusted under 35 U.S.C. 154(b) by 0 days.

(21) Appl. No.: 16/483,879

(22) PCT Filed: Jan. 29, 2018

(86) PCT No.: PCT/RU2018/000037
§ 371 (c)(1),
(2) Date: Aug. 28, 2019

(87) PCT Pub. No.: WO2018/143840
PCT Pub. Date: Aug. 9, 2018

(65) Prior Publication Data
US 2020/0071358 A1 Mar. 5, 2020

(30) Foreign Application Priority Data
Feb. 6, 2017 (RU) .......................... RU2017103887

(51) Int. Cl.
| | | |
|---|---|---|
| *A61K 38/10* | (2006.01) | |
| *A61K 38/00* | (2006.01) | |
| *A61K 9/06* | (2006.01) | |
| *A61P 31/04* | (2006.01) | |
| *A61P 31/10* | (2006.01) | |
| *A61P 31/12* | (2006.01) | |
| *A61P 31/22* | (2006.01) | |
| *C07K 7/08* | (2006.01) | |
| *C07K 7/00* | (2006.01) | |

(52) U.S. Cl.
CPC ................. *C07K 7/08* (2013.01); *A61K 9/06* (2013.01); *A61P 31/22* (2018.01); *A61K 38/00* (2013.01)

(58) Field of Classification Search
CPC .......... A61K 38/00; A61K 38/10; A61K 9/06; A61P 31/04; A61P 31/10; A61P 31/12; A61P 31/22; C07K 7/00; C07K 7/08
USPC .......................... 530/300, 327; 514/1.1, 21.5
See application file for complete search history.

(56) References Cited

PUBLICATIONS

Staubitz et al., "Structure-Function Relationships in the Tryptophan-rich, Antimicrobial Peptide Indolicidin," Journal of Peptide Science, 7: 552-564. (Year: 2001).*
Alexander et al, "Production of novel lipopeptide antibiotics related to A54145 by Streptomyces fradiae mutants blocked in biosynthesis of modified amino acids and assignment of IptK, IlpK and IptL gene functions," The Journal of Antibiotics, 64: 79-87. (Year: 2011).*
Vasilchenko et al., "Antimicrobial activity of the indolicidin-derived novel synthetic peptide In-58," Journal of Peptide Science, 23(12): 855-863. (Year: 2017).*

* cited by examiner

*Primary Examiner* — Julie Ha
(74) *Attorney, Agent, or Firm* — Nadya Reingand; Yan Hankin

(57) ABSTRACT

The invention discloses peptides having biocidal properties, more particularly antibacterial, antifungal, and antiviral properties, and preparations based thereon. A biocidal peptide of general formula Y-Ile-Leu-Pro-X-Lys-X-Pro-X-X-Pro-X-Arg-Arg-NH2, where X is 4-nitrophenylalanine; 4-chlorophenylalanine; 4-methoxyphenylalanine; D-phenylalanine; 4-aminophenylalanine; 4-aminobenzoylphenylalanine; homophenylalanine; 4-tertbutylphenylalanine; 2-methylphenylalanine; 4-fluorophenyl alanine; pentafluorophenylalanine; or 2-trifluoromethylphenylalanine; and Y is H or palmitoyl or aminoundecanoyl, and a preparation in the form of a gel with biocidal properties, containing, as an active substance, the peptide at a concentration of 0.001 to 0.1 wt %. The peptides demonstrate biocidal properties towards bacteria, including spore-forming bacteria, mold fungi, and viruses. The peptide-based gels can be used for treating bacterial and viral infectious diseases and infectious comorbidities.

2 Claims, No Drawings
Specification includes a Sequence Listing.

SEQUENCE LISTING

<160> NUMBER OF SEQ ID NOS: 1

<210> SEQ ID NO 1
<211> LENGTH: 14
<212> TYPE: PRT
<213> ORGANISM: Artificial Sequence
<220> FEATURE:
<223> OTHER INFORMATION: Synthesized
<220> FEATURE:
<221> NAME/KEY: Variant
<222> LOCATION: (1)..(1)
<223> OTHER INFORMATION: Xaa = hydrogen, or palmitoyl, or
      aminoundecanoyl
<220> FEATURE:
<221> NAME/KEY: Variant
<222> LOCATION: (5)..(5)
<223> OTHER INFORMATION: Xaa = 4-nitrophenylalanine, or
      4-chlorophenylalanine, or 4-methoxyphenylalanine, or
      D-phenylalanine, or 4-aminophenylalanine, or
      4-aminobenzoylphenylalanine, or homophenylalanine, or
      4-tert-butylphenylalanine, or 2-methylphenylalanine, or
      4-fluorophenylalanine, or pentafluorophenylalanine, or
      2-trifluoromethylphenylalanine
<220> FEATURE:
<221> NAME/KEY: Variant
<222> LOCATION: (7)..(7)
<223> OTHER INFORMATION: Xaa = 4-nitrophenylalanine, or
      4-chlorophenylalanine, or 4-methoxyphenylalanine, or
      D-phenylalanine, or 4-aminophenylalanine, or
      4-aminobenzoylphenylalanine, or homophenylalanine, or
      4-tert-butylphenylalanine, or 2-methylphenylalanine, or
      4-fluorophenylalanine, or pentafluorophenylalanine, or
      2-trifluoromethylphenylalanine
<220> FEATURE:
<221> NAME/KEY: Variant
<222> LOCATION: (9)..(10)
<223> OTHER INFORMATION: Xaa = 4-nitrophenylalanine, or
      4-chlorophenylalanine, or 4-methoxyphenylalanine, or
      D-phenylalanine, or 4-aminophenylalanine, or
      4-aminobenzoylphenylalanine, or homophenylalanine, or
      4-tert-butylphenylalanine, or 2-methylphenylalanine, or
      4-fluorophenylalanine, or pentafluorophenylalanine, or
      2-trifluoromethylphenylalanine
<220> FEATURE:
<221> NAME/KEY: Variant
<222> LOCATION: (12)..(12)
<223> OTHER INFORMATION: Xaa = 4-nitrophenylalanine, or
      4-chlorophenylalanine, or 4-methoxyphenylalanine, or
      D-phenylalanine, or 4-aminophenylalanine, or
      4-aminobenzoylphenylalanine, or homophenylalanine, or
      4-tert-butylphenylalanine, or 2-methylphenylalanine, or
      4-fluorophenylalanine, or pentafluorophenylalanine, or
      2-trifluoromethylphenylalanine

<400> SEQUENCE: 1

Xaa Ile Leu Pro Xaa Lys Xaa Pro Xaa Xaa Pro Xaa Arg Arg
1               5                   10

BIOCIDAL PEPTIDE AND PREPARATION BASED THEREON

CROSS-REFERENCE TO RELATED APPLICATIONS

The present patent application is a National stage application from PCT application PCT/RU2018/000037 filed Jan. 29, 2018 which claims priority to Russian patent application RU 2017103887 filed Feb. 6, 2017.

FIELD OF THE INVENTION

The invention relates to the field of medicine, in particular, to novel peptides having biocidal properties, more particularly antibacterial, antifungal, and antiviral properties, and to the preparations based thereupon.

BACKGROUND

The number of antimicrobial drug-resistant causative agents has lately increased, reducing the treatment efficacy of socially significant infectious diseases. Furthermore, a combination of bacterial and viral infections became a significant pathogenic factor, making the task of finding new alternative approaches to their therapy more urgent.

To protect higher eukaryotes from infections, the body is known to activate the secretion of endogenous peptide-based compounds, which are synthesized during processing of precursors as active protective components; moreover, their formation occurs much faster while consuming less energy than the formation of antibodies or specific phagocyte cells. [Mangoni, M. L. Host-defense peptides: from biology to therapeutic strategies//Cell. Mol. Life Sci.-2011.-68.-p. 2157-2159].

Development of drugs based on such endogenic peptide-based compounds is one of the possible solutions to the problem of microorganisms being resistant to existing antibiotics. Such pharmaceuticals are already in use today in medical practice or undergoing clinical trials. [Brogden, N. K., and Brogden, K. A. Will new generations of modified antimicrobial peptides improve their potential as pharmaceuticals?//Int. J. Antimicrob. Agents.-2011.-38.-p. 217-225. Yeung, A. T. Y., Gellatly, S. L., and Hancock, R. E. W. Multifunctional cationic host defense peptides and their clinical applications//Cell. Mol. Life Sci.-2011.-68.-p. 2161-2176].

In particular, the peptides previously created by the authors [RU 2183643, 2002] and having the following general formula:

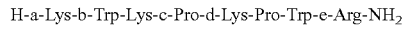

where a=-Ile- or -Lys-; b=-Pro- or -Lys-; c, d=-Lys- or -Trp-; e=Arg or Ala are known in the art. The disadvantage of these peptides is their insufficiently high activity against fungi and viruses.

The structure of indolicidin is the closest to that of the claimed peptide, [Selsted M. E., Novotny M. J., et al/, Indolicidin, a novel bactericidal tridecapeptide amide from neurophils.//J.Biol.Chemistry.-vol. 267.-Jis 7.-1992.-p. 4292-4295] having the following structure:

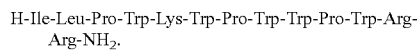

This peptide exhibits an antimicrobial effect on a relatively wide range of bacteria but it is not very effective against viral infections. Another disadvantage of indolicidin is its high hemolytic activity.

A large number of peptide-based dosage forms having a biocidal effect and intended for external use are known in the art. Among them, for example, "Peptide-Active" [http://tiu.ru/Gel-dlya-litsa-s-peptidami.html?no_redirect=1]; the "Body Life" complex [http://lifehappiness.narod.ru/screens/cosmetics/gels.htm]; and hemin derivatives with amino acids and peptides [RU2415868, 2011].

All aforementioned preparations comprise peptide-based active ingredients and excipients.

The disadvantage of said preparations is their relatively low biocidal activity and their typical application as a mixture of naturally occurring peptides, which often doesn't have an exact composition of ingredients.

The closest to the claimed preparation is ALLOMEDIN gel containing the peptide Allostatin as the active ingredient and Carbopol, water, allantoin, phenoxyethanol, ethylhexylglycerin, and sodium hydroxide as excipients. [www.stada.ru/press/ . . . /allomedin-preparat-novogo-pokoleniya-protiv-ge esa-0.html; http://www.biomedservice.ru/price/goods/62/2582].

The disadvantage of this gel is its limited application (only for viral skin infections).

SUMMARY OF THE INVENTION

The objective of the present invention was to develop peptides exhibiting a stronger effect on various groups of microorganisms as well as a finished dosage form for external use based thereupon.

The inventors achieved said objective by developing indolycidin analogs wherein the composition of said analogs characteristically included amino acid residues of phenylalanine derivatives comprising electron-donor and electron-acceptor substituents in the aromatic rings thereof.

The claimed peptides are represented by general formula:

Y-Ile-Leu-Pro-X-Lys-X-Pro-X-X-Pro-X-Arg-Arg-NH2, wherein

X=4-nitrophenylalanine-Phe(NO2), or 4-chlorophenylalanine-Phe(Cl), or 4-metoxyphenyl alanine-Phe(OCH3), or D-phenylalanine-D-Phe, or 4-aminophenylalanine-(4-NH2)Phe, or 4-aminobenzoylphenylalanine-(4-NHBz)Phe, or homophenylalanine-homoPhe, or 4-tert-butylphenylalanine-(4-Bu$^t$)Phe, or 2-methylphenylalanine-(2-Me)Phe, or 4-fluorophenyl alanine-(4-F)Phe [[4-fluoromethylalanine-(4-F)Phe]], or pentafluorophenylalanine-Phe(F5), or 2-trifluoromethylphenylalanine-(2-CF3)Phe, and Y=H, or -palmitoyl-Pal, or aminoundecanoyl-HN2—(CH2)10—CO—.

Said peptides are prepared by a standard solid-phase peptide synthesis technique [J. M. Steward and J. D. Young, "Solid Phase Peptide Synthesis", W.H. Freeman Co., San Francisco, 1969] followed by cleavage of protective groups and purification of the final product. In solid-phase synthesis, tert-butylcarbonyl groups are used for intermediate protection of a-amino groups of amino acids. Arginine's guanidino groups were blocked with mesitylene sulfonyl or nitro groups and ε-amino groups in lysine were protected with 2-clorobenzycarbonyl.

The peptide chain was elongated with 1-hydroxybenzotriazole esters followed by neutralization. Ninhydrin test or bromophenol blue (proline) was used to confirm the completion of the reaction. The peptides were cleaved from the resin and the protective groups were removed with hydrogen fluoride in the presence of scavengers. The synthesized peptides were purified with reverse-phase high performance liquid chromatography (HPLC) under high pressure. The purity of the obtained preparation was more than 95%. All of them showed a satisfactory amino acid analysis and correct mass-spectrometry data.

The structures of the synthesized peptides are shown n Table 1.

TABLE 1

Primary structure of the obtained indolicidin analogs

| Structure | cipher |
|---|---|
| Indolicidin H-Ile-Leu-Pro-Trp-Lys-Trp-Pro-Trp-Trp-Pro-Trp-Arg-Arg-$NH_2$ | 1 |
| $NH_2$—$(CH_2)_{10}$—CO-Ile-Leu-Pro-D-Phe-Lys-D-Phe-Pro-D-Phe-D-Phe-Pro-D-Phe-Arg-Arg-$NH_2$ | 2 |
| H-Ile-Leu-Pro-Phe($NO_2$)-Lys-Phe($NO_2$)-Pro-Phe($NO_2$)-Phe($NO_2$)-Pro-Phe($NO_2$)-Arg-Arg-$NH_2$ | 3 |
| H-Ile-Leu-Pro-Phe(Cl)-Lys-Phe(Cl)-Pro-Phe(Cl)-Phe(Cl)-Pro-Phe(Cl)-Arg-Arg-$NH_2$ | 4 |
| H-Ile-Leu-Pro-Phe($OCH_3$)-Lys-Phe($OCH_3$)-Pro-Phe($OCH_3$)-Phe($OCH_3$)-Pro-Phe($OCH_3$)-Arg-Arg-$NH_2$ | 5 |
| H-Ile-Leu-Pro-D-Phe-Lys-D-Phe-Pro-D-Phe-D-Phe-Pro-D-Phe-Arg-Arg-$NH_2$ | 6 |
| H-Ile-Leu-Pro-(4-$NH_2$)Phe-Lys-(4-$NH_2$)Phe-Pro-(4-$NH_2$)Phe-(4-$NH_2$)Phe-Pro-(4-$NH_2$)Phe Arg-Arg-$NH_2$ | 7 |
| H-Ile-Leu-Pro-(4-NHBz)Phe-Lys-(4-NHBz)Phe-Pro-(4-NHBz)Phe-(4-NHBz) Phe-Pro-(4-NHBz)Phe-Arg-Arg-$NH_2$ | 8 |
| H-Ile-Leu-Pro-homoPhe-Lys-homoPhe-Pro-homoPhe-homoPhe-Pro-homoPhe-Arg-Arg-$NH_2$ | 9 |
| H-Ile-Leu-Pro-(4-Bu')Phe-Lys-(4-Bu')Phe-Pro-(4-Bu')Phe-(4-Bu')Phe-Pro-(4-Bu') Phe-Arg-Arg-$NH_2$ | 10 |
| H-Ile-Leu-Pro-(2-Me)Phe-Lys-(2-Me)Phe-Pro-(2-Me)Phe-(2-Me)Phe-Pro-(2-Me) Phe-Arg-Arg-$NH_2$ | 11 |
| H-Ile-Leu-Pro-(4-F)Phe-Lys-(4-F)Phe-Pro-(4-F)Phe-(4-F)Phe-Pro-(4-F)Phe-Arg-Arg-$NH_2$ | 12 |
| H-Ile-Leu-Pro-Phe($F_5$)-Lys-Phe($F_5$)-Pro-Phe($F_5$)-Phe($F_5$)-Pro-Phe($F_5$)-Arg-Arg-$NH_2$ | 13 |
| H-Ile-Leu-Pro-(2-$CF_3$)Phe-Lys-(2-$CF_3$)Phe-Pro-(2-$CF_3$)Phe-(2-$CF_3$)Phe-Pro-(2-$CF_3$)Phe-Arg-Arg-$NH_2$ | 14 |
| Pal-Ile-Leu-Pro-D-Phe-Lys-D-Phe-Pro-D-Phe-D-Phe-Pro-D-Phe-Arg-Arg-$NH_2$ | 15 |

The conducted experiments showed that the obtained peptides exhibited combined antibacterial and biocidal activity against mold fungi and yeast, as well as against viruses.

A possible mechanism for the peptide bacterial inactivation is attributed to the plurality of micropores forming in the membrane, which results in the equalization of osmotic pressure, release of the contents, and breaking of the nucleotide.

The best results were achieved using 2, 5, and 11 peptides with the following structure:
(2) $HN_2$—$(CH_2)_{10}$—CO-Ile-Leu-Pro-D-Phe-Lys-D-Phe-Pro-D-Phe-D-Phe-Pro-D-Phe-Arg-Arg-$NH_2$
(6) H-Ile-Leu-Pro-D-Phe-Lys-D-Phe-Pro-D-Phe-D-Phe-Pro-D-Phe-Arg-Arg-$NH_2$
(11) H-Ile-Leu-Pro-(2-Me)Phe-Lys-(2-Me)Phe-Pro-(2-Me)Phe-(2-Me)Phe-Pro-(2-Me)Phe-Arg-Arg-$NH_2$ With their high antibacterial activity, which was exhibited in the 1-5 μg/ml dose range, the synthesized peptide didn't induce hemolysis at doses exceeding 200 μg/ml. Moreover, said peptides had an impact on immunocompetent cells. For example, in the 1-10 μg/ml dose range, they produced a statistically significant increase in the spontaneous proliferation of splenocytes and a reduction in the capture of $^3$H-thymidine by spleen cells. During stimulation of the proliferation of splenocytes with lipopolysaccharide (LPS), the peptides at 0.4-2.0 μg/ml doses inhibited the impact of LPS. At 10-0.4 μg/ml doses, they inhibited the NO production, which had been stimulated by LPS, with macrophage cells of the RAW 264.7 line. The specificity of binding the peptides to LPS was additionally confirmed by the fact that the efficiency of the NO production inhibition increased when the stimulating LPS dose decreased.

INDUSTRIAL APPLICABILITY

A preparation for local application based on the synthesized peptides and exhibiting biocidal activity was prepared. The preparation is a clear homogeneous gel for local application free of extraneous particles. The composition of the gel is as follows: (% wt.): active ingredient (peptide)—0.001-0.1; excipients—99.999-99.9. Peptides 2, 6, or 11 are used as active ingredients. Said excipients can be solvents, such as water or water-alcohol solutions, flavorings, antioxidants as well as other substances contributing to the optimal use of the peptide as a biocidal medication. In particular, at least one substance selected from the group comprising Carbopol, allantoin, phenoxyethanol, ethylhexylglycerin, sodium hydroxide, sodium hyaluronate, lavender or castor oil, glycerin, sodium carmellose, citric acid, alpha-tocopherol acetate, benzoic acid, etc. can be included in the composition of the gel as excipients.

The pharmaceutical preparation was prepared following standard procedures for the preparation of dosage forms of pharmaceuticals using a pharmaceutically acceptable peptide salt that doesn't cause adverse local and systemic side effects as the active pharmaceutical ingredient, and appropriate additives providing certain structural viscosity, exhibiting pseudoplastic, plastic and thixotropic properties, and optimizing the bioavailability of the active ingredients.

The practical applicability of the invention is illustrated by the following examples:

EXAMPLE 1

Synthesis of 1 and 3-14 Peptides

The nitro group used to protect the $N^\omega$-function of arginine was ε-amino group of lysine, the chlorocarbobenzoxy group. To synthesize the peptide, 0.2 g of N-tert-butyloxy-carbonyl-$N^\varepsilon$-nitroarginine methylbenzhydryl aminopolymer and 10 ml of dimethylformamide were added to a reaction vessel. The arginine content was 1.0 mmol/g of the polymer. The peptide chain was further elongated from the C-terminus according to the procedure in Table 2.

TABLE 2

Procedure of adding one amino acid residue

| N p/p | Operation | Reagents | Repetition rate | Time, min | Reagent volume, ml |
|---|---|---|---|---|---|
| 1 | Washing | Methylene chloride | 1 | 2 | 10 |
| 2 | Unblocking | 50% trifluoroacetic acid | 1 | 2 | 5 |
| 3 | Unblocking | 50% trifluoroacetic acid | 1 | 30 | 5 |
| 4 | Washing | Dimethylformamide | 3 | 1 | 10 |
| 5 | Neutralization | Diisopropylethylamine (5 mm in dimethylformamide) | 1 | 1 | 5 |
| 6 | Condensation | 1.0 mmol of oxybenzotriazole ester of corresponding amino acid Boc-derivative | 1 | 30 | 5 |
| 7 | Washing | Dimethylformamide | 3 | 1 | 10 |
| 8 | Ninhydrin test/ bromophenol blue-Pro/ | | | | |

If the ninhydrin test was positive, the condensation was repeated starting with p. 3.

Upon completion of the synthesis, the peptidyl-polymer in the reaction vessel was treated with 5 ml of 50% trifluoroacetic acid in methylene chloride, washed with 5 ml of methylene chloride, filtered, removed from the vessel, and transferred to a filter funnel. The product was washed on the filter thrice with 5 ml of isopropyl alcohol portions and thrice with 5 ml of absolute ether portions. The obtained peptidyl-polymer was dried in a vacuum-exicator over phosphorus pentoxide, and 0.2 g of the product was completely unblocked according to the procedure in Table 3.

TABLE 3

Procedure of unblocking peptidyl-polymer and cleaving the peptide from the polymeric matrix

| N p/p | Operation | Reagents | Repetition rate | Time, min | Temperature, °C. | Reagent volume, ml |
|---|---|---|---|---|---|---|
| 1 | Total unblocking and cleavage of the peptide from polymeric matrix | Anhydrous hydrogen fluoride/m-cresol (10:1 by volume) | 1 | 60 | 0 | 5 |
| 2 | Filtration | | | | | |
| 3 | Washing | Absolute ether | 3 | 5 | | 25 |
| 4 | Washing from filter | Trifluoroacetic acid | 3 | — | — | 1 |
| 5 | Precipitation | Diethyl ether | | | | 100 |
| 6 | Filtration | | | | | |
| 7 | Washing | Diethyl ether | 3 | | | 10 |

The obtained crude products were purified by reverse-phase high efficiency chromatography on a C18 Nova Pack, 19×300 mm, 300A° column at 0-7-% acetonitrile gradient in 0.1% trifluoroacetic acid. According to the optical density data, the content of the main substance, the peptides with 1, 3-14 sequences, was at least 98%. The amino acid composition of each peptide and its molecular weight corresponded to the theoretical values. The cumulative analytical parameters of the obtained compounds are shown in Table 4.

EXAMPLE 2

Synthesis of 2 and 15 Peptides

The mesitylenesulfonyl group was used to protect the $N^\omega$-function of arginine. To synthesize the peptide, 0.2 g of N-tert-butyloxycarbonyl-$N^\omega$-mesitylenesulfonyl arginine methylbenzhydryl amino polymer and 10 ml of dimethylformamide were added to a reaction vessel. The peptide chain was further elongated from the C-terminus according to the procedure in Table 2, bonding palmitic acid (15) or Boc-11-aminoundecanoic acid (2) at the last stage.

The obtained peptidyl-polymer was treated with aqueous hydrogen fluoride, and the crude product was isolated according to the technique shown in Table 3. HPLC purification was conducted with an acetonitrile gradient of 12-19% in 0.1% trifluoroacetic acid. Analytical parameters of 2 and 15 peptides are shown in Table 4.

EXAMPLE 3

Biocidal Activity of Synthesized Peptides Against Bacteria

The antimicrobial activity was determined by the radial diffusion method in agarose gels. In the experiment, $4\times10^6$ CFU in the mean logarithmic growth phase were dispersed in 10 ml on a layer of gel (10 mM of sodium phosphate, 0.3 mg of soya broth hydrolysate powder per ml, and 1% (wt/vol) of agarose). Series of peptide dilutions in 0.01% acetic acid containing 0.1% human serum albumin were prepared. 8-μl peptide samples were applied to a layer of gel. Three hours after the peptide application, the top layer was applied (10 ml of soya agar hydrolysate, 60 g/l). Following one night of incubation, the lightened zones were measured with 0.1 mm accuracy. The peptide activity was expressed in relative units of 1 mm=10 U.

MIC was determined as the segment lengths on the regression line X-axis of the zone diameters obtained by serial dilutions of peptide samples. All measurements were made thrice. Test results are given in Table 54.

The obtained results demonstrate that when exposed to bacterial strains, including antibiotic-resistant strains, all the peptides exhibited high biocidal activity, which in some cases exceeded the efficacy of peptide 1 (indolycidin).

The best results were achieved with peptides 2, 6, and 11.

EXAMPLE 4

Biocidal Activity of Synthesized Peptides Against Mold Fungi and Yeast

The antifungal activity was assessed using a technique similar to that of Example 4, using *Candida albicans* 820 strain. The results are shown in Table 6.

Peptides 2, 4, 6, 8, 11, and 13 at 3-10 µg/ml doses were shown to exhibit biocidal activity against mold fungi and yeast, substantially exceeding that of indolycidin.

EXAMPLE 5

Hemolytic Activity of the Obtained Peptides

To determine the hemolytic activity, red blood cells were isolated from the heparinized blood by centrifugation and washed thrice with a barbital/sodium barbital buffer (0.15 M, pH 7.4). The mixture was then diluted with a phosphate (PBS) buffer (0.015 M $Na_2HPO_4$, 0.15 M NaCl, pH 7.4). Samples of peptides in specific concentrations in PBS were placed in wells of a 96-well plate, and a red cell suspension in PBS was added to the samples. The red cell concentration was 1%. PBS was used as the negative control (no hemolysis). The positive control (100% hemolysis) –0.1% triton X-100 in PBS.

The plates were incubated for three hours at 37° C. under 5% $CO_2$ and centrifuged. The supernatant was transferred to a clean plate. The intensity of the hemoglobin release from the destroyed red blood cells was determined on a tablet spectrophotometer "Victor-2" (Finland) at λ-450 nm. $MIH_{50}$ was determined as the lowest concentration, at which 50% hemolysis occurred. All measurements were made thrice. The test results are shown in Table 7.

At high antibacterial activity, which occurred in the 1-5 µg/ml dose range, peptides 2, 6, and 11 didn't induce hemolysis at doses exceeding 200 µg/ml.

EXAMPLE 6

Antiviral Activity of the Obtained Peptides

The following strains were used to assess the peptide effect: H3N2 influenza virus (IV, strain A Pert/16); adenovirus serotype 3 (AV, strain 3/Voronezh/2174/82); and parainfluenza virus, type 3 (HPIV, strain VOK). The influenza virus was received from the virus collection of the Influenza Research Institute of the RAS; the parainfluenza virus and adenovirus were received from the State Collection of Museum Viruses.

Passage cultures of human laryngeal carcinoma cells Hep-2 and MDCK canine kidney cells were used in the study.

1 mg of each preparation was dissolved in 2 ml of DMSO and placed into vials filled with cell-supporting medium (2Eagle MEM and 199 taken in equal proportions) to reach 20.0 µg/ml; 2.0 µg/ml, 0.2 µg/ml, and 0.02 µg/ml final concentrations.

A monolayer of cell cultures was obtained in flasks with the useful area of 25 $cm^2$. Prior to infection, the growth medium was removed and the cell monolayer was washed once with Hank's solution. The passaged culture of HEp-2 cells was infected with adenovirus or parainfluenza viruses type 3 while the MDCK cell culture was infected with the influenza virus; in each case, using a plurality of infections equal to 0.1-0.01 TCID50/cell.

Experiments with uninfected cultures of Ner-2 and MDCK cells were conducted parallel to the experiments with infected samples, in similar flasks. Some of the samples were used as cell control, and others—to determine the possible toxic effect of the preparation on the cells.

The flasks with infected cell cultures were filled with a cell supporting medium (SM) not containing the experimental preparations (virus control) or containing experimental peptides 2,6, and 11, which exhibited the highest activity against bacteria and fungi at 20.0 µg/ml; 2.0 µg/ml, 0.2 µg/ml and 0.02 µg/ml doses. A SM of the same composition was added to the uninfected cell cultures (preparation control). A SM not containing peptides (cell control) was added to the other part of the uninfected cell cultures.

Observations were conducted over 3-4 days, depending on the cytopathogenic effect of the virus in the control flasks (virus control). The possible toxic effect of the preparations on the cells was evaluated daily by microscopy of uninfected cell cultures with the SM containing or not containing the peptides (preparation control). At the end of the observation period, the samples of the virus-containing culture fluid (VCF) were titrated to determine the infectious activity in the experimental and control samples.

For that, 01 ml each of Hep-2 or MDCK cell suspensions, prepared in seed concentrations, were placed in the wells of polystyrene plates marked "for cell culture". 24-48 hrs. after a monolayer was formed, the VCF was added to the culture in a 1:10 to 1:1,000,000 dilution with a coefficient 10 in the growth medium, and 0.1 ml of each dilution were placed into 4 wells of the plate. Six wells were kept as cell controls by adding 0.1 ml of the medium to them. Both infected and control cells were incubated in a thermostat with 5% $CO_2$ in a stationary position at 34.5±0.5° C. Titration results were evaluated after 3 days (influenza virus) or 4 days (parainfluenza, adenovirus) by the presence of a direct cytopathogenic effect (CPE) on the cells caused by the virus.

The activity of the viral reproduction was evaluated by the size of the infection titers calculate by the Reed, Muench method. The results of the antiviral activity study of the preparations are presented in Table 8.

The examined peptides at 20 µg/ml or 2.0 µg/ml doses demonstrated a significant (more than 100-1,000 times) reduction in the infectious activity of H3N2 influenza virus (IV, strain A Pert/16), adenovirus serotype 3 (AV, strain 3/Voronezh/2174/82); and parainfluenza virus type 3 (HPIV, strain VOK). The peptides at a 0.2 µg/ml dose reduced the infectious activity of the influenza virus and adenovirus to a lesser degree, but also statistically significantly (more than 10-100 times).

EXAMPLE 7

Effect of Peptides on Immunocompetent Cells

The effect of the peptides on the spontaneous and mitogen-induced murine thymus and spleen cell proliferation was examined. Murine thymuses were collected under aseptic conditions, homogenized, suspended in RPMI-1640 (Sigma) medium, and filtered through two gauze layers. The resulting cell suspension was washed twice with RPMI-1640 (Sigma) medium and resuspended in RPMI-1640 culture medium containing 2 mM of L-glutamine (Sigma) and 80 µg/ml of gentamycin. The number of cells was calculated in a Goryaev chamber. The cell concentration was brought up to 10×10⁶/ml with the culture medium containing 4% of fetal serum (FCS) (Sigma).

Murine spleens were collected under aseptic conditions, homogenized in RPMI-1640 (Sigma) medium, and filtered through two sterile gauze layers. The resulting homogenate was centrifuged, and red blood cells were then lysed with 0.83% ammonium chloride solution. The splenocytes were washed twice in RPMI-1640 (Sigma). The number of cells was calculated in a Goryaev chamber. The spleen cell concentration was brought up to 5×10⁶/ml in 1 ml of RPMI-1640 (Sigma) medium adding 2 mM of L-glutamine (Sigma), 80 µg/ml of gentamycin, and 20% FCS.

To stimulate the thymus and spleen cell proliferation, a lipopolysaccharide (Sigma) was used at 0.2 and 0.02 µg/ml final concentrations. In vitro studies of the effect of synthetic indolycidin analogs on the lymphocyte proliferation were conducted at different concentrations of the preparations (10 to 0.016 µg/ml concentration range). The experiment was conducted in flat-bottom 96-well test plates (Costar). Cell cultures were incubated at 37° C. under 5% $CO_2$ for 72 hrs. 16 hrs. prior to the end of cultivation, $^3$H-thymidin (Isotope) was added to all the wells at 5 µCi/ml final concentration. When cultivation was over, the cell cultures were harvested and transferred to filters; the filters were dried, and the amount of the captured $^3$H-thymidin was measured on a liquid scintillation counter (Rackbeta 1217). The results were expressed in impulses per minute (imp/min). The data is presented in Tables 9-12.

TABLE 9

Effect of the peptides on spontaneous proliferation of thymus cells

| Peptide | Concentration, µg/ml | | | | Control |
|---|---|---|---|---|---|
| | 10 | 2 | 0.4 | 0.08 | |
| 1 | 311 ± 171 | 348 ± 150 | 213 ± 44 | 175 ± 60 | 268 ± 24 |
| 2 | 211 ± 57* | 249 ± 50 | 321 ± 57 | 273 ± 75 | |
| 6 | 736 ± 161* | 298 ± 63 | 246 ± 48 | 306 ± 103 | |
| 11 | 310 ± 127* | 347 ± 122 | 207 ± 84 | 229 ± 54 | |
| PMB | 201 ± 66 | 197 ± 12 | 197 ± 10 | 255 ± 68 | |

*$p < 0.05$
**$p < 0.01$

TABLE 10

Effect of the peptides on spontaneous proliferation of spleen cells

| Peptide | Concentration, µg/ml | | | | Control |
|---|---|---|---|---|---|
| | 10 | 2 | 0.4 | 0.08 | |
| 1 | 1754 ± 382 | 2552 ± 560 | 2188 ± 690 | 1454 ± 465 | 2016 ± 438 |
| 2 | 1174 ± 282** | 1225 ± 474* | 1791 ± 219 | 2439 ± 526 | |
| 6 | 3279 ± 177** | 1854 ± 236 | 1615 ± 248 | 1530 ± 510 | |
| 11 | 1155 ± 182 | 1849 ± 157 | 2149 ± 474 | 1724 ± 608 | |
| PMB | 2051 ± 456 | 2051 ± 167 | 1548 ± 140 | 1488 ± 497 | |

*$p < 0.05$
**$p < 0.01$

TABLE 11

Effect of the peptides on the proliferation of spleen cells stimulated with LPS (0.02 µg/ml)

| Peptide | Concentration, µg/ml | | | | Control |
|---|---|---|---|---|---|
| | 10 | 2 | 0.4 | 0.08 | |
| 1 | 2763* ± 122** | 2269* ± 711* | 4738* ± 228* | 5231* ± 1141 | 5984 ± 1426 |
| 2 | 2443* ± 1316* | 3970 ± 936** | 4008 ± 524 | 4827 ± 1013 | |
| 6 | 3322 ± 818** | 4085 ± 480** | 6431 ± 114 | 4526 ± 1720 | |
| 11 | 1109 ± 1316** | 2600 ± 462* | 5065 ± 2547** | 5570 ± 1378 | |
| PMB | 1644 ± 374** | 2083 ± 321** | 3604 ± 618** | 4404 ± 310* | |

*$p < 0.05$
**$p < 0.01$

TABLE 12

Effect of the peptides on the proliferation of spleen cells stimulated with LPS (0.2 µg/ml)

| Peptide | Concentration, µg/ml | | | | Control |
|---|---|---|---|---|---|
| | 10 | 2 | 0.4 | 0.08 | |
| 1 | 11245 ± 909** | 14065 ± 2013* | 19555 ± 1700 | 18239 ± 4420 | 5984 ± 1426 |
| 2 | 2726* ± 2041** | 10389 ± 613** | 13289 ± 997** | 17121 ± 2647 | |
| 6 | 14637 ± 1047** | 24419 ± 3610* | 20901 ± 845* | 17812 ± 1977 | |
| 11 | 4943 ± 1502** | 14313 ± 2421 | 20849 ± 4226 | 17419 ± 5213 | |
| PMB | 4526 ± 967** | 6450 ± 670** | 11376 ± 2718** | 15840 ± 1260 | |

*$p < 0.05$
**$p < 0.01$

RAW-264.7 line cells were cultivated for 16 hrs. in the wells of a 48-well plate in $1\times10^6$/ml concentration, at 0.5 ml per well in DMEM/F-12 (Sigma) culture medium with 2 mM of L-glutamine (Sigma), 80 µg/ml of gentamycin, and 10% FCS in a $CO_2$ incubator. Upon completion of incubation, the culture medium in all wells of the plate was replaced with 0.25 ml of fresh medium. The experimental preparations at 40, 8, and 1.6 µg/ml concentrations were preincubated with LPS (0.8 and 0.16 µg/ml) for two hours in a $CO_2$ incubator. Polymixin B (Calbiochem) (PMB) in the same concentrations was used as the positive control of the inhibition of the LPS effect. The prepared mixture was then added at 0.25 ml increments to the wells of the culture plate at least in two parallel experiments. A mixture of LPS and the culture medium was added to the control wells. The cells were cultivated for 24 hrs. in a $CO_2$ incubator. NO production was measured based on the total nitrite level in the culture medium in the Greiss test by using a commercial reagent (Sigma) according to the manufacturer's specifications. The results are presented in Tables 13-14.

TABLE 13

Effect of the peptides on NO production by RAW 264.7 macrophage line cells stimulated with 0.2 ml of LPS (NO production inhibition in %)

| Peptide | Concentration, µg/ml | | |
|---|---|---|---|
| | 10 | 2 | 0.4 |
| 1 | 20 | 0 | 3 |
| 2 | 84 | 23 | 2 |
| 6 | 7 | 10 | 1 |
| 11 | 30 | 9 | 3 |
| PMB | 98 | 62 | 11 |

TABLE 14

Effect of the peptides on NO production by RAW 264.7 macrophage line cells stimulated with 0.04 ml of LPS (NO production inhibition in %)

| Peptide | Concentration, µg/ml | | | |
|---|---|---|---|---|
| | 10 | 2 | 0.4 | 0 |
| 1 | 36 | 0 | 0 | |
| 2 | 94 | 52 | 16 | |
| 6 | 8 | 1 | 0 | |
| 11 | 52 | 12 | 7 | |
| PMB | 94 | 85 | 44 | |

2,6, and 11 peptides made an impact on immunocompetent cells. For instance, at the 2-10 µg/ml dose range, they showed a statistically significant enhancement of the spontaneous proliferation of splenocytes and a reduction in the of $^3$H-thymidine inclusion by spleen cells. When splenocyte proliferation was stimulated with a lipopolysaccharide, the peptides at 0.4-2.0 µg/ml doses inhibited the LPS effect. Moreover, at 10-0.4 µg/ml doses, they inhibited the NO production, stimulated by LPS, with RAW 264.7 macrophage line cells. The specificity of the peptides binding with LPS was also confirmed by the fact that the efficiency of the NO production inhibition increased when the stimulating LPS dose decreased.

EXAMPLE 8

Preparation of Gel for the Prevention and Treatment of Skin and Mucousa Diseases A chemical reactor with a stirrer is used to prepare the gel. The gel components are loaded into the mixer in the following formulation (wt. %): Carbopol (1.5-2.0%), distilled water, and NaOH solution (1.5-2.0%); then stirred, allowed to stand for 30 min, titrated with citric acid solution to pH 6, and, while stirring, combined with portions of the aqueous peptide solution containing methylparaben in the amount of 0.01-0.2 wt. % and propylparaben in the amount of 0.002-0.01 wt. % as preservatives. 1.5-2.5 wt. % of glycerin is added to the obtained mixture. The system is stirred for 10 min. and the pH is measured. The obtained homogeneous gel is left to mature for 24 hrs. The gel is then stirred again, and the homogeneous mass is packed into containers (tubes).

The result is a transparent homogeneous gel for external (local) application free of foreign particles. The gel has the following composition (wt. %): peptide—0.001-0.1 and auxiliary additives—99.999-99.9. The characteristics of the obtained gel preparations comprising peptides are shown in Table 15.

TABLE 15

Composition of gel preparations comprising peptides

| Sample | Active ingredient | | Excipients, wt. % (water-rest) | | | |
|---|---|---|---|---|---|---|
| | Peptide | Concentration Wt. % | Carbopol | Methylparaben | Propylparaben | Glycerin |
| 2m | 2 | 0.001 | 1.5 | 0.2 | 0.01 | 2.5 |
| 2c | 2 | 0.01 | 1.7 | 0.1 | 0.01 | 2.0 |
| 2b | 2 | 0.1 | 2.0 | 0.01 | 0.002 | 1.5 |
| 6m | 6 | 0.001 | 1.5 | 0.2 | 0.01 | 2.5 |
| 6c | 6 | 0.01 | 1.7 | 0.1 | 0.01 | 1.9 |
| 6b | 6 | 0.1 | 2.0 | 0.01 | 0.002 | 1.5 |
| 11m | 11 | 0.001 | 1.5 | 0.2 | 0.2 | 2.5 |
| 11c | 11 | 0.01 | 1.7 | 0.1 | 0.1 | 1.7 |
| 11b | 11 | 0.1 | 2.0 | 0.01 | 0.002 | 1.5 |

EXAMPLE 9 Antiviral Activity of Peptide-Based Preparations Against Human Herpes Simplex Virus, Type 2, in Experiments In Vivo Three groups of animals, containing 15 subjects each, were formed to conduct the experiment.

Group 1: infected with type 2 herpes simplex virus and using the peptide preparations (experimental group).

Group 2: infected with type 2 herpes simplex virus and using Acyclovir (preparation control).

Group 3: infected with type 2 herpes simplex virus and not using pharmaceutical preparations (virus control).

Experimental infection with herpesvirus. Type 2 herpes simplex virus, strain G (ATCC VR-734, USA), was used in the experiment. The virus was cultivated in T98G cell culture (human brain glioblastoma), then adapted to mice by two consecutive intracerebral passages in mice of different groups. To prepare the final infective material, the animals were intracerebrally infected with brain tissue from the second passage; on the $4^{th}$ day post infection, the animals were euthanized, their brain was extracted, a homogenate was prepared, used to infect Vero cells, and incubated for 48 hours at 37° C. under 5% $CO_2$ using the culture fluid, in which the infectious titer of the virus was previously determined, as the infectious material.

Zovirax (Acyclovir as 5% ointment, Glaxo Welcome) was used as a comparator drug.

The murine vaginal epithelium was injured with a scarifier for vaginal smears, after which the animals in groups 1 and 2 were infected with 30 μl of the virus at a $10^6$ $TCID_{50}$ dose. The preparations were applied to the wounds per the following regimen: once a day 1, 2, 3, 4, and 5 days post infection.

The animals were followed for 18 days. The cessation of mortality was determined by the absence of mice with the signs of herpetic vaginitis (vaginal discharge) and complications thereof (posterior limb paresis) in the murine groups. Deaths of the animals in the control and experimental groups were recorded daily. Based on the mortality data for each group, the mortality rate (Mr, the ratio of the fallen animals at the time of control to the total number of infected animals in the group), protective index (IP, the ratio of the difference in the percentage of mortality in the control and experimental groups to the percentage of mortality in the control group), and the average life span of the animals (ALS) per each day of the experiment were calculated per the following formulas:

The protective activity of the peptides was assessed by the reduction in the specific mortality and increase in the life span of the animals compared to the control group that wasn't treated. The protective activity data is shown in Table 16.

TABLE 16

Protective activity of the preparations in lethal herpes infection caused in mice by vaginal infection with type 2 herpes simplex virus (n = 15)

| Preparation | # Animals in group | Number of Dead animals | Number of Survived animals | ALS, 24 hrs. | Mortality, % | Protective index, % | Increase in ALS |
|---|---|---|---|---|---|---|---|
| 1 | 15 | 9 | 6 | 12.1 | 60.0 | 18.1 | 0.8 |
| 2m | 15 | 8 | 7 | 12.8 | 53.3 | 27.2 | 1.5 |
| 2c | 15 | 5 | 10 | 13.6 | 33.3 | 54.5 | 2.3 |
| 2b | 15 | 5 | 10 | 13.7 | 33.3 | 54.5 | 2.4 |
| 6m | 15 | 8 | 7 | 12.2 | 53.3 | 27.2 | 0.9 |
| 6c | 15 | 8 | 7 | 12.6 | 53.3 | 27.2 | 1.3 |
| 6b | 15 | 8 | 7 | 12.8 | 53.8 | 26.6 | 1.5 |
| 11m | 15 | 7 | 8 | 12.7 | 46.6 | 22.8 | 1.4 |
| 11c | 15 | 6 | 9 | 13.0 | 40.0 | 45.4 | 1.7 |
| 11b | 15 | 6 | 9 | 13.2 | 40.0 | 45.4 | 1.9 |
| Acyclovir | 15 | 4 | 11 | 13.9 | 26.7 | 63.6 | 2.5 |
| Virus control | 15 | 11 | 4 | 11.3 | 73.3 | — | 0.0 |

The best results were obtained with 2c and 2b preparations.

The conducted studies demonstrated that the claimed peptides exhibited biocidal activity against bacteria, including spore-forming, mold fungi, and also viruses. The best results were obtained for 2, 4, and 11 peptides. Peptide-based gels can be used for the treatment of bacterial, viral, and comorbidities.

What is claimed is:

1. A biocidal peptide of general formula,
Y-Ile-Leu-Pro-X-Lys-X-Pro-X-X-Pro-X-Arg-Arg-NH$_2$,
where X comprises a phenylalanine derivative, said phenylalanine derivative being selected from one of: 4-nitrophenylalanine, 4-chlorophenylalanine, 4-methoxyphenylalanine, 4-aminophenylalanine, 4-aminobenzoylphenylalanine, homophenylalanine, 4-tert-butylphenylalanine, 2-methylphenylalanine, 4-fluorophenylalanine, pentafluorophenylalanine, or 2-trifluoromethylphenylalanine, and
where Y=NH$_2$—(CH$_2$)$_{10}$—CO.

2. A preparation in a form of a gel with biocidal properties containing a peptide as an active ingredient and excipients, wherein said preparation comprises the biocidal peptide according to claim 1 at 0.001 to 0.1 wt. % concentrations.

* * * * *